United States Patent [19]

Shimada et al.

[11] 4,273,636

[45] Jun. 16, 1981

[54] SELECTIVE CHEMICAL SENSITIVE FIELD EFFECT TRANSISTOR TRANSDUCERS

[76] Inventors: Kiyoo Shimada; Makoto Yano, both of 1660, Sakazu, Kurashiki; Kyoichiro Shibatani, 1000-107, Hajima, Kurashiki; Tsutomu Makimoto, 1660, Sakazu, Kurashiki, all of Japan

[21] Appl. No.: 907,729

[22] Filed: May 19, 1978

[30] Foreign Application Priority Data

May 26, 1977 [JP] Japan .................................. 52-62445
May 26, 1977 [JP] Japan .................................. 52-62446
May 26, 1977 [JP] Japan .................................. 52-62447

[51] Int. Cl.³ ...................... G01N 27/30; G01N 27/40
[52] U.S. Cl. ............................... 204/195 P; 128/635; 357/25; 435/817
[58] Field of Search ......... 357/25; 204/195 P, 195 M; 128/635; 324/29; 435/817

[56] References Cited

U.S. PATENT DOCUMENTS

| | | | |
|---|---|---|---|
| 3,719,576 | 3/1973 | Macur | 204/195 P |
| 4,020,830 | 5/1977 | Johnson et al. | 128/2 E |
| 4,053,381 | 10/1977 | Hamblen et al. | 204/195 M |

OTHER PUBLICATIONS

Jiri Janata et al., Biomedical Engineering, pp. 241–245, Jul. 1976.
Masayoshi Esashi et al., J. Japan Soc. of Applied Physics, vol. 44, pp. 339–343, (1975).
Stanley D. Moss et al., Anal. Chem., vol. 47, No. 2, pp. 2238–2243, Nov. 1975.

Primary Examiner—G. L. Kaplan

[57] ABSTRACT

A chemical sensitive field effect transistor transducer is provided having a semipermeable membrane on the surface of a chemical selective system overlying an insulated gate field effect transistor. Such a field effect transistor transducer is effective for the measurement of chemical constituents of factory waste water containing micro-particles, saliva or blood containing proteins, etc., where conventional devices give unreliable results.

12 Claims, 3 Drawing Figures

SELECTIVE CHEMICAL SENSITIVE FIELD EFFECT TRANSISTOR TRANSDUCERS

BACKGROUND OF THE INVENTION

1. Field of the Invention

This invention relates to a field effect transistor (FET) transducer having a chemical selective system overlying the insulated gate region which has a stabilizing system on the gate surface. The transducer of this invention is stable and reliable for uses such as the measurement of concentrations of various kinds of ions, gases, enzymes, substrates, antigens, antibodies and substances which are selectively adsorbed and/or absorbed.

2. Description of the Prior Art:

There has been a continuing search for means of measurement of various chemical substances such as hydrogen ion, sodium ion, potassium ion, calcium ion, chloride ion, oxygen gas, carbon dioxide gas, carbon monoxide gas, sulfur dioxide gas, nitrogen oxide gases, various hydrocarbons and so on, not only in chemical laboratories but also in the waste water or exhaust fumes of various factories or in the exhaust fumes of car motors. Also, such measurements have become quite important in the field of medicine. Generally, it is desirable in most of those cases to carry out measurements continuously and multitudinously. For such purpose, chemical selective electrodes are employed, where it is desired to detect and/or measure electrochemically ionic concentration, redox potential, adsorption of any substances and so on.

For the measurement of ion activity or concentration, various ion electrodes have been conveniently adopted. For example, hydrogen ion, sodium ion, potassium ion, calcium ion, chloride ion, carbon dioxide, ammonia, etc. are measured according to this technique. The principle of this technique as well as the types of chemical substances measured by this method are disclosed in "Selective Ion Sensitive Electrodes", by G. J. Moody and J. D. R. Thomas (Merrow Publishing Co., Ltd., Watford, England, 1971). Thus, a glass electrode is a convenient tool for continuous measurements of the concentrations of the various chemical substances mentioned above, using various selective chemical sensitive membranes. Such electrodes, however, are limited in the following ways. (1) When the resistance of a glass membrane is as high as about 10 M ohm, amplifiers designed to work with such an electrode must possess high input impedance. (2) The mechanical strength of such electrodes is very low. (3) When such an electrode is miniaturized, high membrane resistance resulting from the small area of the glass membrane brings about difficulty in electric insulation and, therefore, poor stability in its operation. (4) Integration of such an electrode for multiple channel purposes results in impractical bulkiness.

Other prior art apparatus disclosed in "Development, Operation and Applications of the Ion-Sensitive Field Effect Transistor as a Tool for Electrophysiology" by Piet Bergveld, IEEE Transactions of Biomedical Engineering, 1972, 342, includes a new type of electrode where a semiconductor is employed and those limitations found in the above-mentioned electrodes are avoided. Bergveld indicated therein the measurement of hydrogen and sodium ion activities in aqueous solution with the use of a metal oxide semiconductor field effect transistor (MOSFET) modified by removal of the gate metal, i.e., an insulated gate FET having silicon oxide as the gate insulating layer on its gate region. This FET transducer has several excellent practical advantages; it is feasible for super-miniaturization without influencing output impedance as well as for integration of various transducers where multiple sensors are prepared on one tiny silicon piece. One problem with the device of Bergveld is that the insulated gate layer comprises silicon oxide and therefore the immersion of the transducer in an aqueous solution results in continuation of the hydration process of the silicon oxide insulation layer. This, of course, affects the accuracy of the ion activity measurement and may also result in electrical leakage of the device.

Those limitations found in the device of Bergveld have been overcome by T. Matsuo and K. D. Wise, as disclosed in "An Integrated Field Effect Electrode for Biopotential Recording", IEEE Transactions on Biomedical Engineering BME-21, 1974, 485. The device disclosed therein comprises a silicon nitride layer overlying a silicon oxide layer in the insulated gate region, the latter being the same as that disclosed by Berveld. This structure of the insulated gate layer results in the prevention of the hydration process of the silicon oxide layer and therefore enables a stable measurement of hydrogen ion activity. Moreover, Matsuo and Wise suggested therein that their device would be further extended to transducers sensitive to various chemical substances, although they did not describe a specific structure.

A device designed to measure various chemical substances is disclosed in U.S. Pat. No. 4,020,830. The device described therein comprises selective chemical sensitive systems, similar to those of the glass electrode, overlying the insulated system of the gate region. Thus, the application of various selective chemical sensitive layers on the insulated gate region enabled the FET transducers to detect or measure selectively antigens, antibodies, hormones, enzymes, reducible gases, and the like, as well as various ions. Seemingly, the devices described therein are promising as sensors of the future as they are usable to measure various chemical substances by applying various selective chemical systems sensitive to any substances of interest on the insulated gate region. Also, the amplifiers to be utilized with the devices are rather simple in structure and are manufactured inexpensively when compared with those needed for glass electrodes. Also, they have advantages such as feasibility of super-miniaturization, mass-production, etc., which are inherent features of transistors.

It was, however, discovered by the present inventors that such FET transducers did not provide stable and reliable measurements and were not sufficiently convenient for practical use for various reasons. First of all, when a non-selective interaction such as adsorption or precipitation on the surface of the gate region takes place, it often disturbs its output signal, often by as much as 1-2 units on the pH scale. For example, non-selective interactions were found to disturb the measurement of FET transducers in factory waste water and in body fluid due to non-selective precipitation of floating micro-particles and adsorption of protein on the gate surface, respectively. This resulted in many problems such as instability of measurement, signal drift, etc., when used for long periods. Secondly, FET transducers are sensitive to light, yielding electromotive force with light-illumination, which results in experimental error, electronic noise, and therefore less accurate measurement. This problem, of course, can be avoided when the transducer is used in a dark room or with a dark cover to shut out light. It is obvious that such a procedure is annoying and impractical for a general purpose transducer. The present invention is directed to overcoming the above-mentioned problems which are important for practical use and, as a result, an FET transducer is provided that permits stable and reliable measurement. Thus, the present invention made it feasible to put FET transducers to practical use, in the monitoring of factory waste water and exhaust fumes, in various industrial instruments and in laboratory experiments, as well as in measurement and monitoring of chemical constituents contained in blood, cerebrospinal fluid, tears, urine, lymph, and the like. In the latter types of measurement, the small size and disposability (ease of massproduction) of FET transducers made possible by photo-engraving techniques make them most advantageous compared to conventional measuring devices.

SUMMARY OF THE INVENTION

It is an object of the present invention to provide an improved FET transducer which permits stable and accurate measurements.

It is another object of the present invention to provide an FET transducer that yields accurate measurements in blood, cerebrospinal fluid, tears, lymph, and the like.

It is also an object of the present invention to provide a device that has prolonged stability, reliability and operational readiness when used in vivo in the form of an indwelling catheter sensor.

It is still another object of the present invention to provide a transducer which is insensitive to light and stable during operation in the presence of light.

The above and other objects of this invention will become apparent from the following detailed description of the invention.

The above-mentioned objects may be accomplished in the present invention by coating a semipermeable organic membrane on the surface of a selective chemical sensitive system on the insulated gate region of an FET transducer and by hydration of the applied membrane before use.

DETAILED DESCRIPTION OF THE PREFERRED EMBODIMENTS

Figure 1:
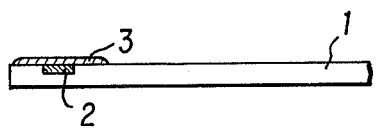
FIG. 1 is a schematic view of an example of an FET transducer of the present invention.

The principle feature of an FET is its ability to control current flow between source and drain with the magnitude of electric potential on the surface of the insulated gate. The invention of Bergveld and Matsuo and Wise was the discovery of the feasibility of ion concentration measurement as current flow between drain and source, which is controlled by ion concentration when an appropriate system to interact with the ion is present on the surface of the insulated gate layer. In order to prepare various ion sensors based on their discoveries, selection of a selective chemical sensitive system which interacts selectively with the ion of interest and correlatively to its concentration in a test solution is essential, and many of such selective chemical sensitive systems have been developed in the field of conventional electrode technology. By using such conventional selective chemical sensitive membranes, the present inventors have investigated the preparation of various FET transducers selectively sensitive to hydrogen ions, sodium ions, potassium ions, and the like, which are able to measure the concentration of the ion of interest in a solution containing various other ions. During the course of this investigation, it was also discovered that not only ions but also varieties of substances such as chemical substances having a dipole moment could induce the field effect when adsorbed on the surface of the insulated gate system. This finding suggested the possibility of preparing FET transducers to sense varieties of chemical substances. On the other hand, however, it presented a serious problem relating to the practical use of FET transducers. Namely, it must be utilized in such a way that no substance except that of interest, e.g., hydrogen ion, which could influence the current flow between drain and source is adsorbed, interacted and desorbed on the surface of the selective chemical sensitive system when in use. For example, the hydrogen ion FET transducer of the invention of Matsuo and Wise can be operated quite successfully in ordinary waters, buffer solutions, etc., and is not influenced by non-selectively interacting substances. Nevertheless, when used in factory waste water containing floating micro-particles, saliva containing various proteins and serum having various substances, it was found that the same FET transducer as mentioned above showed a drift in its output signal during measurement and provided extremely different readings from those obtained by a conventional glass electrode, the deviation of one from the other being as much as 1-2 units on the pH scale. This clearly demonstrated the influence of precipitation of floating micro-particles and adsorption of bio-protein on the surface of the selective chemical sensitive system of the FET transducer. Such precipitation of micro-particles and adsorption of bio-protein may occur in the case of glass electrodes as well, but they do not disturb its output reading. It therefore appears that instability and/or unreliability of measurements due to non-selective precipitation or adsorption as mentioned above is an inherent problem with FET transducers. The present inventors have discovered that coating the selective chemical sensitive system of FET transducers with a semipermeable membrane makes the transducer stable for use in factory waste water having floating micro-particles, body-fluid containing protein, etc. Seemingly, the presence of a semipermeable membrane on the surface of the gate region can prevent the approach of substances which may precipitate or interact non-selectively while it does not prevent the approach of substances which the selective chemical sensitive system is designed to detect. Under these conditions, field effects due to nonselective adsorption, interaction or precipitation on the surface of the selective chemical sensitive system, if present at all, have a negligibly small effect on the conducting channel between source and drain, owing to the large distance of such non-selective interactions from the surface of the selective chemical sensitive system. In practice, most of the semipermeable membranes described herein have structures such that non-target substances do not interact and precipitate non-selectively on their surfaces.

The semipermeable membranes adopted in the present invention are organic polymer membranes which do not react or interact with most substances, and which have similar physical and chemical structures to those of conventional dialysis membranes, ultra-filtration (U.F.) membranes, reverse osmosis (R.O.) membranes and micro-filters. They are such that substances of interest (e.g., hydrogen ions, sodium ions, potassium ions etc.) may permeate the membranes and those substances which interfere with the measurement (e.g., polymers such as protein) do not permeate when placed in the solution of interest. The application of such membranes to the surfaces of the sensing systems of FET transducers brings about accurate and reliable measurement, since adsorption or interaction, even though they take place, do not induce field effects on the conducting channel. The membranes of this invention can be both hydrophilic membranes or porous hydrophobic membranes. Suitable hydrophilic membranes have a water content more than 10%, and preferably in the range of 20–90%. A lower water content than 10% lengthens the response time and causes signal drift. The water content of the present invention is defined as $(W_1-W_2)/(W_1+W_2)$, where a sample membrane is prepared under exactly the same conditions as those used to prepare the semipermeable membrane on the surface of the sensing region, and the weight of membrane weighed after water on the membrane is wiped away is $W_1$ and the weight of the membrane in absolute dryness is $W_2$. That is, the water content of the present invention is a property pertaining to the membrane itself and does not denote the actual content of water in the membrane which is coated on the FET transducer. In general, however, it is the content of water in the membrane on the transducer, since it is immersed in an aqueous system when in use.

The hydrophilic membrane of the present invention is exemplified by those made of poly-ether, poly-acrylate, poly-methacrylate, cellulose, gelatin, poly-maleic acid and various other organic polymers, and preferably those of hydrophilic poly-methacrylate such as poly-$\beta$-hydroxyethylmethacrylate (poly-HEMA) and poly-$\beta$-dimethylaminoethylmethacrylate, poly-acrylamide, poly-vinylpyridine, poly-vinylpyrrolidone, poly-vinylalcohol (PVA), etc. (These polymers may be either homopolymers or copolymers with the other comonomers.) Among them, poly-HEMA and PVA are especially preferred when the test solution of interest is blood. Here, the poly-HEMA may be a homopolymer or a copolymer with hydrophilic comonomers such as hydroxypropylacrylate and those expressed by the general formula: $CH_2=C(R)COO-(CH_2CH_2O)_n-R'$ (R being —H or —$CH_3$, R' being aryl, alkyl, —$CH_2CH_2OH$, —$NH_2$, —$NHCH_3$, —$N(CH_3)_2$, —$N(CH_3)_3$, n being an integer), hydrophobic comonomers such as styrene, methylmethacrylate etc., crosslinkable monomers such as ethyleneglycoldimethacrylate, glycidylmethacrylate etc., or comb-like copolymers where hydrophobic polymers such as poly-styrene and poly-methylmethacrylate are grafted on a trunk polymer of poly-HEMA. In order to improve their bio-compatibility, they may be heparinized. Introduction of a hydrophobic group or a crosslinking group may result in an increase of the mechanical strength when swollen in water. The degree of polymerization of said polymer should be more than 100. Here, the content of hydrophobic groups or crosslinking groups should be such that the water content is not less than 10%, since a greater content of such groups increases the response time excessively. The homopolymer of PVA is preferably heat-treated to increase the wet mechanical strength and copolymers with hydrophobic comonomers such as ethylene etc. may be used as well. The hydrophilic membrane in the present invention may form a so-called hydrogel containing 20–90% water. Thus, the substance of interest may permeate the membrane toward the sensing surface of the FET transducer while polymeric substances such as protein do not permeate the membrane.

On the other hand, a suitable porous hydrophobic membrane is such that the water content is more than 10% and the cut-off molecular weight is less than 20,000 where the cut-off molecular weight denoted herein is the molecular weight which characterizes molecules whose rejection by the membrane is more than 90%. Membranes which fulfill such conditions may include acetylcellulose, nitrocellulose, poly-vinylchloride, poly-amide, poly-ester, poly-carbonate, poly-tetrafluoroethylene, etc.

Methods used to prepare such membranes on the surface of FET transducers are as follows. Hydrophilic membranes may be formed by coating an appropriate solution of said polymer followed by evaporation of the solvent (dry method). There are no limitations with respect to solution temperature, rate of solvent evaporation and so on. Porous hydrophobic membranes may be formed by a wet method, where coating of the polymer solution is followed by a coagulation process in a non-solvent bath, as well as a dry method or a dry-wet joint method. Here, the polymer solvent and, for the coagulation bath, the temperature of the polymer solution and the coagulation bath, and the rate of solvent evaporation are all appropriately chosen. Also, it is preferred that said membrane may be crosslinked by photo-irradiation of a potassium dichromate containing membrane or heat treatment of a glutaraldehyde containing membrane, where the crosslinking agent may be added either before or after the membrane is formed.

On the other hand, when a transducer may be used under light illumination, its output signal may be easily influenced by the light. The problem associated with this light sensitivity has been alleviated by darkening the above-mentioned semipermeable membranes on the gate region, and such transducers have produced stable measurements under various conditions of light illumination. The term "darkening" means that the average optical density when measured perpendicular to the surface using light of 350 nm–700 nm wavelengths is more than 0.7, and no serious effects are to be expected when the darkness is less than this value. Such dark membranes may be prepared by dissolving or dispersing a dye or pigment in the polymer or monomer solution from which the membrane is cast, as well as by dying the membrane after it has already been prepared on the transducer. It is most preferred to form a dark membrane from a polymer solution containing a dispersed pigment therein such as carbon black. Such light-stabilized transducers produce stable measurements in places where light density changes from time to time.

Transducers stabilized according to said procedure still must be calibrated occasionally with buffer solutions of known pH, since initial drift due to gate surface hydration takes place. It is, however, not practical to calibrate the transducer frequently when used in vivo and it is therefore advantageous to prevent initial drift. This may be attained by stabilization of the surface structure of the selective chemical sensitive system of the transducer toward hydration as known in the conventional glass electrode. Several different processes may be used to achieve such stabilization of the surface structure toward hydration, and these processes may be practiced at any time between the time when the transistor is prepared and when it is used in practice. A suitable solution to perform said process has to contain water and its content is preferably more than 50% of the total amount. Besides water, it may contain various salts as pH stabilizers. The transducer thus stabilized is already ready-to-use and can show stable measurement without any initial drift in an aqueous system. The same result can be observed even when it is left in air for about one week after it has been stabilized. When it is left in air for too long a period, such as more than several months, or is exposed to high heat, however, the surface of the selective chemical sensitive system may again be destabilized toward water and, when used in water next time, exhibit initial drift. Such a transducer can be stabilized again according to the aforementioned procedure. Advantageously, it is preferred to store the stabilized transducer in a container together with the stabilizing solution so that the stabilized surface of the transducer may be maintained as it is. Since the FET transducer becomes ready-to-use when stored in such a container, this type of packaging is especially preferred for distribution to users.

Figure 2:
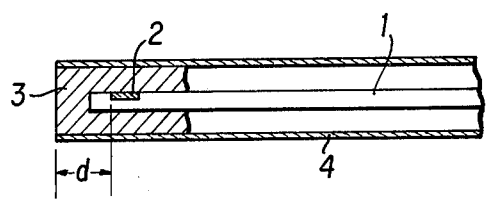
FIG. 2 is a schematic view of another example of an FET transducer of the present invention.

FIG. 1 shows an example of a membrane coating on the surface of an FET gate region. A polymer layer (3) is formed around the gate region (2) of the FET transducer (1). FIG. 2 shows an embodiment of the present invention wherein a hydrophilic polymer membrane (3) is coated between the gate region (2) and the inside wall of a catheter (4). The thickness of the membrane, d, is preferably in the range $0.1\mu$ to 5 mm, where d is defined to be the shortest distance from the gate surface to the membrane surface (membrane surface denoting the surface in contact with the solution). When the membrane is thinner than $0.1\mu$, not only is the mechanical strength too low but also substances adsorbed on the membrane surface may induce field effects. On the other hand, when it is thicker than 5 mm, not only does the response time become impractically long but the size of the device may have to be expanded, which is undesirable in view of the trend towards miniaturization.

Due to the ease of miniaturization and integration of plural transducers through the use of photo-engraving techniques, the FET transducer of the present invention may be most advantageous especially when the amount of test solution is limited or the system to be tested is extremely small. This may be the case when the measurements are carried out in cell culture solutions, nmr samples, body fluids, etc. The body fluids may be exemplified by plasma, serum, saliva, cerebrospinal fluid, ascites, urine, tears, and blood containing an anticoagulative reagent.

In such body fluids, where measurements of plural constituents are preferred, integration of multi-channel transducers may enable the otherwise unattainable simultaneous measurement of these constituents. Also, ease of miniaturization may minimize trauma to the living body to a large extent and therefore may provide a practical invasive monitoring sensor. Of course, when used in blood, further measures may be needed in order to prevent coagulation of the blood.

The following examples are illustrative of the present invention. FET transducers for hydrogen and sodium ions were prepared according to the procedure of Matsuo and Wise, and measurements were carried out by recording the potential difference between gate and source ($V_{GS}$) while the potential difference between drain and source ($V_D$) and current flow ($I_D$) in the conducting channel are kept constant, as in the case of Matsuo and Wise.

EXAMPLE 1

On the surface of the gate region of a hydrogen ion FET transducer having a silicon nitride layer as the selective chemical sensitive system, a $20\mu$ thick membrane was formed by first coating with an 8% ethanolic solution of poly-$\beta$-hydroxyethylmethacrylate (poly-HEMA) and then drying the coating at room temperature overnight. The poly-HEMA coated transducer as well as a non-coated one were immersed in distilled water overnight at room temperature in order to accomplish the hydration process. A commercial glass pH electrode was used as reference. These three transducers were calibrated using buffer solutions of pH 6.88 and pH 9.22 before experiments in tap water and four kinds of body fluids, the results of which are collected in Table 1. These three transducers reproducibly showed exactly the same values when tested in tap water. In the case of body fluids, however, the membrane coated FET transducer reproducibly exhibited the same value as that obtained with the glass electrode while the non-coated one showed a different value, indicating the failure of its measurement. The water content of the membrane in this experiment was 74%.

TABLE 1 pH in various solutions.

| Sample | Glass Electrode | FET Transducer uncoated | p-HEMA coated |
|---|---|---|---|
| Tap water | 6.31 | 6.31 | 6.31 |
| Human Saliva | 6.95 | 7.18 | 6.96 |
| Human Serum | 7.30 | 7.78 | 7.32 |
| Human ACD Blood | 6.80 | 7.49 | 6.83 |
| Human Whole Blood, heparinized | 7.30 | 8.19 | 7.29 |

EXAMPLE 2

On the surface of the gate region of a hydrogen ion FET transducer having a silicon nitride layer as its selective chemical sensitive system, a membrane was formed by immersing the transducer in an ethanol solution containing 2% carbon black, 15% of a copolymer of 10% $\beta$-hydroxyethylacrylate and 90% $\beta$-hydroxyethylmethacrylate and 0.2% potassium dichromate, followed by drying in air and then heat treatment at 100° C. The pH transducer was then boiled in water for about 2 hours. Using the thus prepared transducer, pH measurements of factory waste water were carried out. After one week of continuous experimentation, it was found that the transducer indicated the same pH value as that obtained by a glass electrode which was tested at the same time, despite white precipitation which had grown on the dark membrane.

EXAMPLE 3

Figure 3:
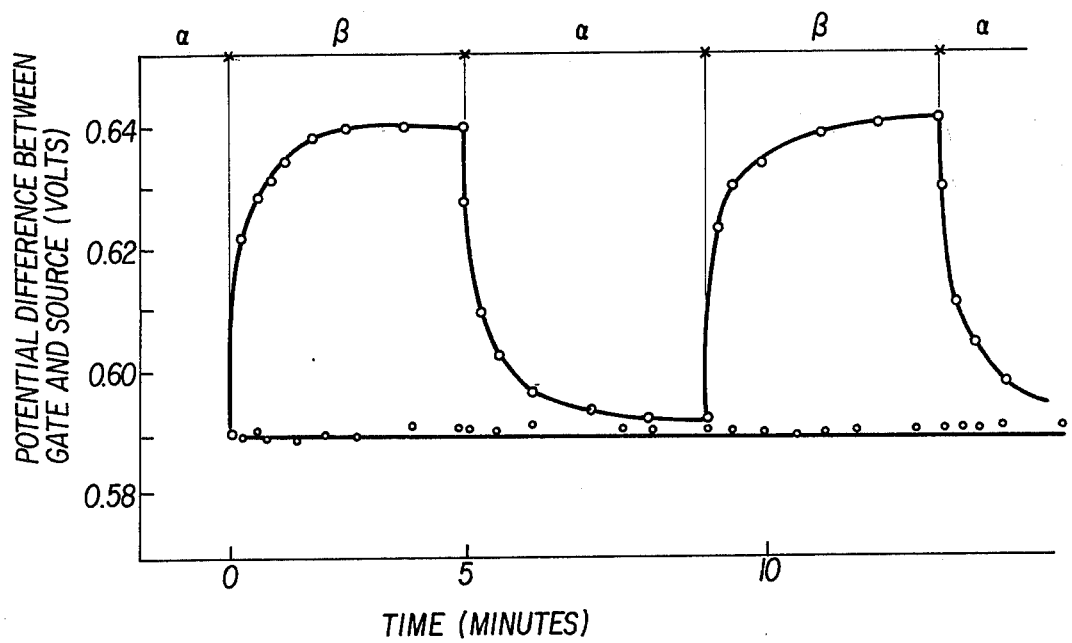
FIG. 3 is an experimental graph obtained when an FET transducer of the present invention was immersed in blood.

On the surface of the gate region of a pH FET transducer having a silicon nitride layer as its selective chemical sensitive system, a membrane about $20\mu$ thick was formed by coating with an 8% ethanolic solution of poly-HEMA followed by drying at room temperaure overnight. After the coated transducer was immersed in distilled water for 24 hours, measurements were carried out in dog ACD blood (pH 6.9) and in a buffer solution of the same pH value (pH 6.9). Here, $I_D$ was 30μ A, $V_{DS}$ was 2.0 V and $V_{GS}$ was recorded, where a $V_{GS}$ of 55 mV corresponds to one unit on the pH scale. The result is depicted in FIG. 3, where α and β refer to buffer solution and ACD blood respectively and the water content of the poly-HEMA membrane was 74%. It is clearly revealed that the poly-HEMA coated transducer (b) gave stable measurements while the non-coated one (a) gave gradually increased $V_{GS}$ values when immersed in blood. The poly-HEMA coated transducer showed the same $V_{GS}$ value as that of the non-coated one in the buffer solution.

EXAMPLE 4

Poly-HEMA-MMA copolymers having different degrees of swelling were prepared in ethanol with various feed-monomer ratios. From either acetone or ethanols solutions of these copolymers, membranes of about 20μ thickness were prepared according to the procedure in EXAMPLE 1. Using these transducers, measurements in dog ACD blood were carried out in order to study response times as a function of water content, where response time is the time required to attain the average value of $V_{GS}$ at pH 7.0 and $V_{GS}$ at pH 8.0 when the transducer was transferred from one to the other. The results are collected in Table 2. It is clearly shown that, when the water content of the membrane is less than 10%, the response time increases rapidly and the measurement becomes unreliable.

TABLE 2

Response time and signal drift.

| Feed Monomer (%) | | Water Content | Response Time | Signal Drift |
|---|---|---|---|---|
| HEMA | MMA | (%) | (sec) | in Dog ACD Blood |
| 100 | 0 | 74 | 10 | none |
| 80 | 20 | 53 | 15 | none |
| 60 | 40 | 46 | 30 | none |
| 40 | 60 | 19 | 120 | none |
| 20 | 80 | 9.5 | 1600 | none |
| 10 | 90 | 5.0 | >10000 | unmeasurable |
| 0 | 100 | 1.0 | >10000 | unmeasurable |

EXAMPLE 5

On the surface of the gate region of a pH FET transducer having silicon nitride as the selective chemical sensitive system, a porous acetylcellulose membrane was formed as follows. A solution having a mixture of 17 parts of acetyl cellulose, 69.2 parts of acetone, 1.45 parts of $Mg(ClO_4)_2$ and 12.35 parts of water was coated on the gate surface, and a membrane was formed by evaporating part of the solvent, followed by immersing the transducer in water at 0° C. and gelling the membrane therein. After washing with water and then treating in hot water of 70° C., a porous membrane was obtained. The transducer was further immersed in water overnight before use. The measurement of $V_{GS}$ was carried out in blood containing heparin, which is used to prevent blood coagulation, and in a buffer solution, the pH value of which was the same as that of the blood. The results are collected in Table 3, where $I_D = 30$ μA and $V_{DS} = 2$ V.

TABLE 3

$V_{GS}$ of FET transducer in various solutions.

| | non-coated transducer | coated transducer |
|---|---|---|
| Blood, heparinized | −1.983 V | −1.932 V |
| Buffer solution | −1.932 V | −1.932 V |

It is clearly demonstrated that the acetyl cellulose membrane coated transducer yielded stable, reliable and accurate values, while the non-coated transducer showed a gradual drift to lower values of $V_{GS}$ in heparinized blood: the equilibrated value was about 50 mV less than that found in the buffer solution.

What is claimed as new and intended to be secured by letters patent is:

1. A selective chemically sensitive FET transducer which selectively detects specific chemical substances to which the transducer is exposed, which comprises:
an FET transducer whose gate region is overlayed with a chemically selective sensitive membrane, which reacts or interacts with a specific chemical substance(s) and which is provided with a semipermeable membrane having a water content greater than 10% overlying said chemically selective sensitive membrane, said semipermeable membrane consisting of a hydrophillic membrane material(s) or a hydrophobic membrane material(s), each of said maerial(s) containing a light darkening dye or pigment.

2. The transducer of claim 1, wherein said semipermeable membrane is prepared by dissolving or dispersing a light darkening dye or pigment in the polymer or monomer soluion from which said membrane is cast.

3. The transducer of claim 2, wherein said pigment is carbon black.

4. The transducer of claim 1, wherein said semipermeable membrane is dyed after it has been cast on said surface of the gate region.

5. A selective chemically sensitive FET transductor which selectively detects specific chemical substances to which the transducor is exposed, which comprises:
an FET transducer whose gate region is overlayed with a chemically selective sensitive membrane, which reacts or interacts with a specific chemical substance(s) and which is provided with a semipermeable membrane having a water content greater than 10%, overlying said chemically selective sensitive membrane, said semipermeable membrane being formed of a hydrophilic material selected from the group consisting of a polymethacrylate, a polyacrylate, a polyacrylamide, a polyvinylpyrrolidone, a polyvinyl alcohol and copolymers thereof.

6. The transducer of claim 1 or 5, wherein the thickness of said semipermeable membrane is between 0.1μ and 5 mm.

7. The transducer of claim 1 or 5, wherein the average optical density of said semipermeable membrane using light of 350 nm to 700 nm wavelength is more than 0.7 when measured perpendicular to the surface.

8. The transducer of claim 1 or 5, wherein said semipermeable membrane is heparinized.

9. The transducer of claim 1, wherein said semipermeable membrane is formed of a hydrophilic material selected from the group consisting of a polymethacrylate, a polyacrylate, a polyacrylamide, a polyvinylpyrrolidone, a polyvinylalcohol and copolymers thereof.

10. The transducer of claim 5 or 9, wherein said membrane is a hydrogel containing 20–90% water.

11. The transducer of claim 5 or 9, wherein said semipermably membrane material is poly-β-hydroxyethyl methacrylate.

12. The transducer of claim 5 or 9, wherein the said semipermeable membrane material is a copolymer formed from β-hydroxyethylmethacrylate and comonomers selected from the group consisting of hydroxypropyl acrylate, acrylate or methacrylate esters having the formuls $CH_2=C(R)COO-(CH_2CH_2O)_nR'$, wherein R is H or $CH_3$ and R' is aryl, alkyl, $-CH_2CH_2OH$, $-NH_2$, $-NHCH_3$m $-N(CH_3)_2$, $-N(CH_3)_3+$, and n is an integer, styrene, methyl methacrylate ethylene glycol dimethacrylate, glycidyl methacrylate, and graft copolymers of poly-styrene or poly-methyl methacrylate on poly-β-hydroxyethyl methacrylate.

\* \* \* \* \*

UNITED STATES PATENT AND TRADEMARK OFFICE
CERTIFICATE OF CORRECTION

PATENT NO. : 4,273,636
DATED : Jun. 16, 1981
INVENTOR(S) : KIYOO SHIMADA ET AL

It is certified that error appears in the above—identified patent and that said Letters Patent is hereby corrected as shown below:

On the cover sheet Insert:

[73]--Assignees:

KURARAY COMPANY, LIMITED
Okayama Pref. 710    JAPAN

*Signed and Sealed this*

*Twenty-ninth* Day of *September 1981*

[SEAL]

*Attest:*

*Attesting Officer*

GERALD J. MOSSINGHOFF

*Commissioner of Patents and Trademarks*